United States Patent
Liu et al.

[11] Patent Number: 6,110,454
[45] Date of Patent: Aug. 29, 2000

[54] PROCESS FOR MAKING SUBSTANTIALLY HOMOGENEOUS COPOLYMERS OF VINYL PYRROLIDONE AND N-3,3-DIMETHYLAMINOPROPYL METHACRYLAMIDE FOR PERSONAL CARE APPLICATIONS

[75] Inventors: Kou-Chang Liu, Wayne; Lowell R. Anderson, Morristown; Eugene E. Hardy, East Brunswick; Yakir Reuven, West Orange, all of N.J.

[73] Assignee: ISP Investments Inc., Wilmington, Del.

[21] Appl. No.: 08/655,492

[22] Filed: May 30, 1996

Related U.S. Application Data

[62] Division of application No. 08/365,258, Dec. 28, 1994, Pat. No. 5,609,865.

[51] Int. Cl.[7] ............................. A61K 31/79; C08F 2/10; C08F 226/10; C08F 220/60
[52] U.S. Cl. ........................ 424/78.32; 523/303; 523/305; 526/264; 526/328.5
[58] Field of Search .................... 424/78.32; 526/264, 526/328.5; 523/303, 305

[56] References Cited

U.S. PATENT DOCUMENTS 4,923,694  5/1990  Shih et al. .

*Primary Examiner*—Edward J. Webman
*Attorney, Agent, or Firm*—Walter Katz; William J. Davis; Marilyn J. Maue

[57] ABSTRACT

A process is described for making substantially homogeneous copolymers comprising 20–99% of vinyl pyrrolidone (VP) and 1–80% of N-3,3-dimethylaminopropyl methacrylamide, (DMAPMA), preferably 50–95% VP and 5–50% DMAPMA, and, most preferably, about 80:20, by weight, having a weight average molecular weight of about 200,000 to 1,500,000, as a clear, low viscosity aqueous solution of the homogeneous copolymer, at a 5–20% solids level, preferably about 10–15%, by weight of the solution, having a viscosity of about 5,000 to 80,000 cps, preferably about 10,000 to 70,000 cps. The solution obtained herein has lower viscosity and better clarity, and provides hair care products with enhanced curl retention (hold), when compared to non-homogeneous copolymers of the same composition, or related existing commercial products.

10 Claims, 2 Drawing Sheets

PROCESS FOR MAKING SUBSTANTIALLY HOMOGENEOUS COPOLYMERS OF VINYL PYRROLIDONE AND N-3,3-DIMETHYLAMINOPROPYL METHACRYLAMIDE FOR PERSONAL CARE APPLICATIONS

This is a division, of application Ser. No. 08/365,258, filed Dec. 28, 1994, now U.S. Pat. No. 5,609,865.

BACKGROUND OF THE INVENTION

1. Field of the Invention

This invention relates to a process for making substantially homogeneous copolymers of vinyl pyrrolidone (VP) and N-3,3-dimethylaminopropyl methacrylamide (DMAPMA) of predetermined composition and clear, low viscosity aqueous solutions thereof, for use in hair styling and hair care applications.

2. Description of the Prior Art

Several synthetic polymers containing vinyl lactams are presently being used in cosmetic formulations, particularly in hair care products, to contribute body, set retention and conditioning to such products.

Representative of the art in this field are the following U.S. Pat. Nos. 3,914,403; 3,954,960; 4,057,533; 4,210,161; 4,586,518; 4,753,793; 4,764,363; 4,834,968; 4,842,850; 4,902,499; 4,906,459; 4,923,694; 4,963,348; 4,983,377; 5,011,895 and 5,015,708; and WO 91/15186; WO 91/15185; EPO 0412704A2; EPO 0412707A1; and JP 57126409.

Generally these synthetic polymers were made by a "one-pot" polymerization process in which selected amounts of the several monomers were reacted together. The composition of these one-pot polymers was considered as being the same as the composition of the charged monomers. However, in reality, such a polymerization process can provide only a mixture of polymers of various compositions, and, additionally, an indeterminate amount of homopolymers and undesired copolymers.

Accordingly, it is an object of this invention to provide a process for making substantially homogeneous copolymers of vinyl pyrrolidone (VP) and N-3,3-dimethylaminopropyl methacrylamide (DMAPMA).

Another object of this invention is to provide a clear, low viscosity aqueous solution of homogeneous copolymers of VP and DMAPMA, in a compositional range of 20–99% VP and 1–80% DMAPMA, preferably 50–95% VP and 5–50% DMAPMA, and most preferably about 80% VP and 20% DMAPMA, at a solids level of 5–20%, preferably 10–15%, by weight of the solution, having a viscosity of about 5,000 to 80,000 cps, preferably about 10,000 to 70,000 cps.

Still another object herein is to provide clear, low viscosity aqueous solutions of substantially homogeneous copolymers of VP and DMAPMA in a predetermined compositional range and at a selected solids level, which, upon formulation into hair styling compositions, will provide enhanced conditioning, fixative and hair holding properties for the user.

SUMMARY OF THE INVENTION

A process is described herein for making substantially homogeneous copolymers of 20–99% vinyl pyrrolidone and 1–80% N-3,3-dimethylaminopropyl methacrylamide, preferably about 50–95% VP and 5–50% DMAPMA, and most preferably about 80% VP and 20% DMAPMA, by weight, having a weight average molecular weight of about 200,000 to 1,500,000, and a clear, low viscosity aqueous solution of the homogeneous copolymer at a 5–20% solids level, preferably about 10–15%, by weight of the solution, and having a viscosity of about 5,000 to 80,000 cps, preferably about 10,000 to 70,000 cps.

The copolymer solution obtained herein is less viscous and has better clarity than solutions of non-homogeneous copolymers of the same composition, or of related commercial products. When formulated into hair styling compositions, these homogeneous polymer solutions also provide improved curl retention (hold) during use.

DETAILED DESCRIPTION OF THE INVENTION

Figure 1:
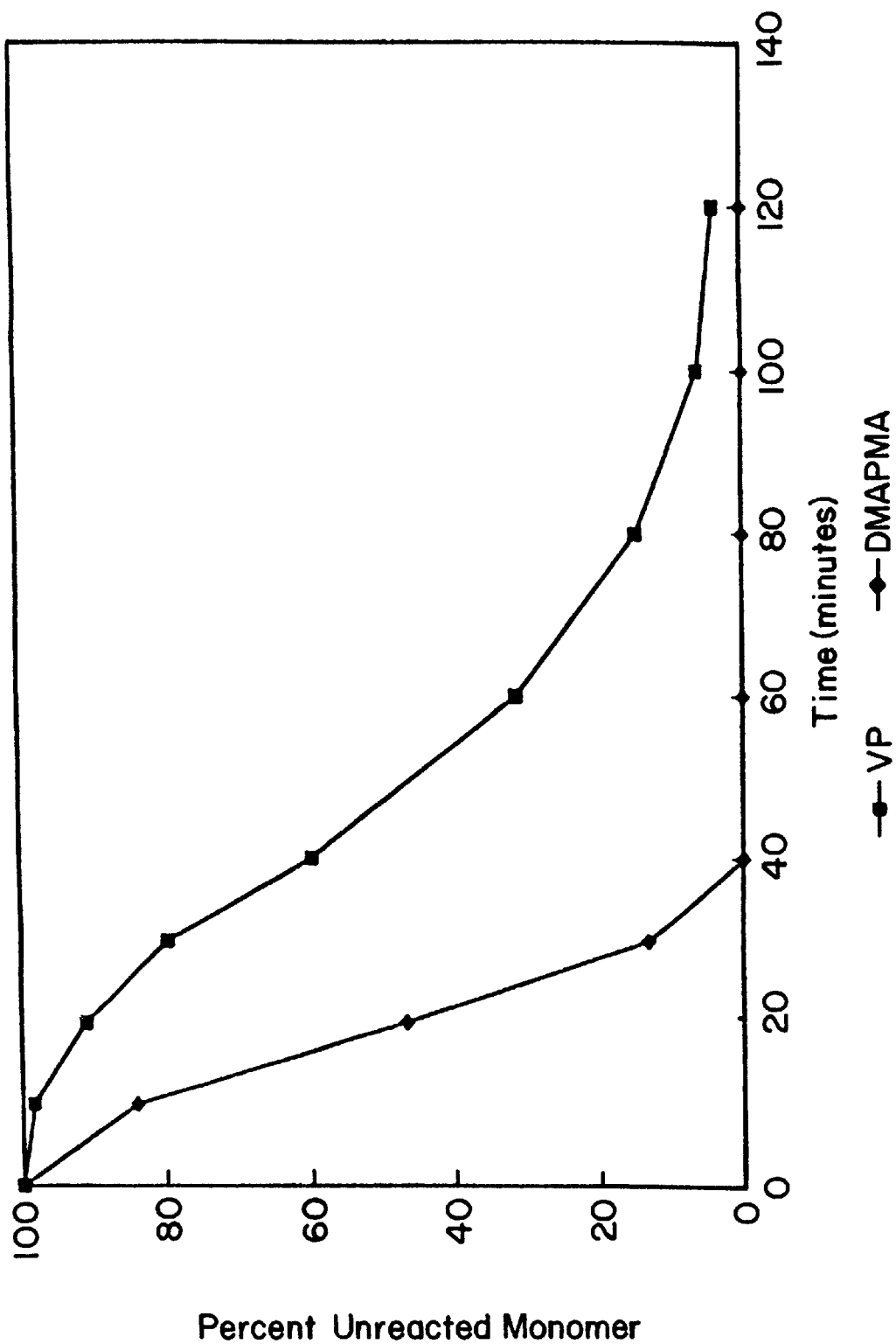
FIG. 1 is a graphical representation of a non-homogeneous (one-pot) process in which is plotted percent unreacted VP and DMAPMA vs. time for a reaction mixture of 80:20% by weight VP/DMAPMA copolymer at 15% solids.

In accordance with the present invention, a process is provided for making substantially homogeneous copolymers of vinyl pyrrolidone and N-3,3-dimethylaminopropyl methacrylamide of predetermined composition.

In this process, the less reactive monomer of the copolymer (VP) is precharged into a reactor at a suitable reaction temperature, generally about 50–80° C., preferably 55–75° C. Then the more reactive monomer (DMAPMA) is introduced incrementally into the VP-charged reactor at a rate which corresponds to the observed rate of disappearance of VP.

The entire predetermined amount of the DMAPMA monomer is added before substantially all the VP monomer has been consumed so that both monomers can react to form a substantially homogeneous copolymer in a desired compositional ratio of VP:DMAPMA. Consequently, a copolymer is obtained whose composition approaches the nominal monomer ratio of the desired copolymer composition and whose structure has the two individual monomeric units of the copolymer distributed substantially uniformly in a homogeneous chain along the backbone of the polymer. For example, for an 80:20 weight ratio of VP/DMAPMA copolymer, which is approximately equivalent to a 6:1 mole ratio of VP/DMAPMA, the homogeneous copolymer of the invention has a monomer distribution corresponding substantially close to VP-VP-VP-VP-VP-VP-DMAPMA-VP-VP-VP-VP-VP-VP-DMAPMA . . . .

The precharge in the process of the invention may include some DMAPMA therein, generally in an amount which is less than 10% of the total amount of DMAPMA required for the predetermined copolymer composition without affecting the homogeneous polymerization process. However, it is still necessary that the rate of addition of DMAPMA after any precharge is carried out at substantially the rate of disappearance of VP during copolymerization.

The schedule of addition of DMAPMA to accomplish the desired matched rate of reaction of VP is determined in the following manner.

DETERMINATION OF ADDITION SCHEDULE FOR DMAPMA TO FORM A HOMOGENEOUS COPOLYMER OF VP AND DMAPMA

A. First, a one-pot copolymerization of VP and DMAPMA was carried out as follows:

EXAMPLE 1

VP (215 g), DMAPMA (54 g), and deionized water (1530 g) were charged into a 2-liter resin pot equipped with a gas inlet, a liquid inlet, a thermometer and a condenser. A stream of nitrogen then was bubbled through the solution and maintained during the reaction. The solution was gradually heated to 68° C.; then 0.25 ml of Lupersol 11 (t-butylperoxy pivalate) as catalyst was added; then another 0.25 ml of the catalyst was added after 10 minutes; and another 6 units of 0.25 ml was added each 30 minutes. The total addition was carried out over a 4-hour period.

The relative percentage amounts of residual monomers present during the course of the one-pot reaction was determined by gas chromatographic analysis after sampling the reaction mixture periodically. The analytical data obtained then was plotted as the graph of FIG. 1

As shown in FIG. 1, DMAPMA reacts much more rapidly than VP. Accordingly, after 240 minutes, all the DMAPMA is consumed while residual VP monomer still is available for homopolymerization. Thus the copolymer formed is of a composition different from the desired monomer ratio selected by the precharged amounts of the two monomers. Under these experimental conditions, the polymer product obtained is a complex mixture of a homopolymer which is polyvinylpyrrolidone, and a copolymer of VP and DMAPMA of uncertain composition.

B. To form a homogeneous copolymer, it is necessary that the curve of rate of reaction vs. time for DMAPMA substantially coincide or match the rate of reaction curve for VP. To accomplish this, the VP is precharged and substantially all the DMAPMA is fed after to the precharge at a feeding schedule determined by analysis of the data of FIG. 1. The % DMAPMA monomer to be fed at time t of the polymerization is determined from the Asymmetric Double Sigmoidal Distribution formula, $A_t$, below, which has four adjustable parameters, $a_1$, $a_2$, $a_3$ and $a_4$:

$$A_t = \frac{1}{1 + \exp\left[\frac{a_1 - \frac{a_2}{2} - t}{a_3}\right]} \left[1 - \frac{1}{1 + \exp\left[\frac{a_1 + \frac{a_2}{2} - t}{a_4}\right]}\right]$$

where t=time in minutes during copolymerization;
  $a_1$ is a parameter which determines the center of the distribution;
  $a_2$ is a parameter which affects the width of the distribution;
  $a_3$ is a parameter which determines the ascending portion of the distribution; and
  $a_4$ is a parameter which determines the descending portion of the distribution.

$$\% DMAPMA \text{ to be fed at time } t = \frac{A_t}{\sum_{t=0}^{N} A_t} \times 100$$

where N=time when the polymerization is completed.

To match the DMAPMA curve to the VP curve of FIG. 1, an "initial guess" is made for the values of $a_1$, $a_2$, $a_3$ and $a_4$.

These values are inserted into the $A_t$ formula and the % DMAPMA to be fed at time t is calculated. Then a polymerization reaction is carried out using this schedule. The resulting % unreacted DMAPMA during this polymerization will probably not match the % unreacted VP at the same time t. If the % unreacted DMAPMA at time t is too large, then the value of $a_3$ (ascendancy) in the $A_t$ formula is increased, $a_4$ (descendency) is decreased, $a_1$ (center) is decreased, and $a_2$ (width) is decreased. Conversely, if the initial guess values of $a_1$ through $a_4$ give a reaction rate for DMAPMA which is too fast, then changes in the values of $a_1$ through $a_4$ are made in a direction opposite to those discussed above.

These new values of the parameters are then used to determine a new feeding schedule. Using this feeding schedule, another polymerization is carried out, and the process of adjustment of the parameters described above is repeated.

This process is known as "interative fitting" of data to a curve. After 4 or 5 such iterative fittings, the experimental VP and DMAPMA curves will be matched to a satisfactory degree, as shown in FIG. 2 herein.

Figure 2:
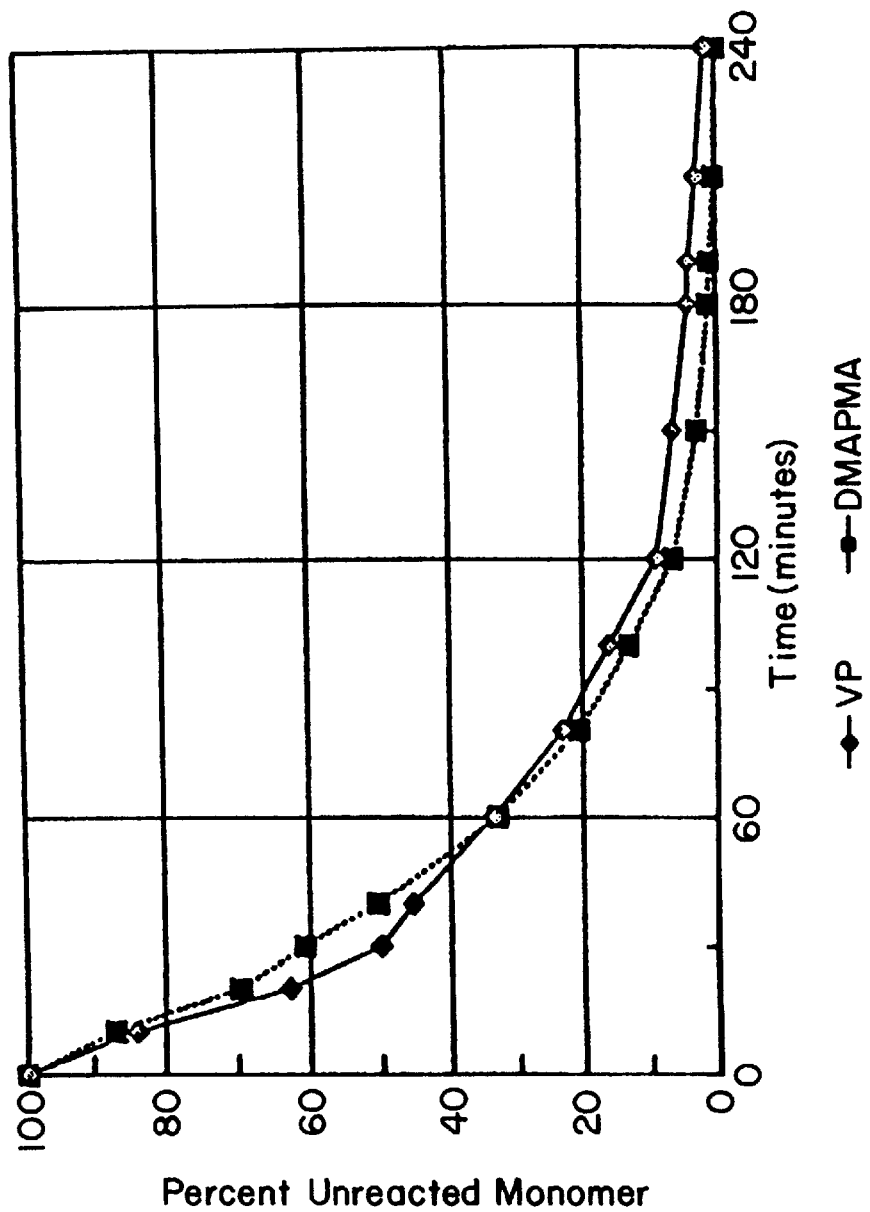
FIG. 2 is a graphical representation of the homogeneous process of the invention in which is plotted percent unreacted VP and DMAPMA vs. time during the preparation of an aqueous solution of 80:20% by weight VP/DMAPMA copolymer at 15% solids.

The matching curve of DMAPMA in FIG. 2 can originate from at least one set of values for $a_1$, $a_2$, $a_3$ and $a_4$ (the last set of the iterative fitting process) used to calculate a suitable feeding schedule of DMAPMA over the entire period of the polymerization. One such set is:

$a_1$=17
  $a_2$=28
  $a_3$=2
  $a_4$=40

C. With such a suitable DMAPMA feeding schedule available, a homogeneous copolymer of VP and DMAPMA was prepared as described in Example 2 below.

EXAMPLE 2

In this example, residual monomers were monitored as in Example 1.

Preparation of a Homoaeneous Copolymer of VP and DMAPMA

In this process, 216 grams of vinylpyrrolidone (recrystallized material) and 580 grams of deionized water were charged to a 2-liter water jacketed resin flask.

The flask was equipped with an overhead stirrer connected to an anchor stirrer, a nitrogen inlet for sparging to remove dissolved air and a thermocouple which is connected to a temperature controller. The temperature was raised to 68° C., by passing heated water from a temperature controlled bath into the jacket of the resin flask. A mechanical syringe pump which could be set to deliver DMAPMA at a set rate was connected to the reactor through polyethylene tubing.

The DMAPMA reactant was added from the syringe pump as a 1 liter solution of 54 grams of DMAPMA in water, according to the following feeding schedule:

| Time (min.) | Amount of DMAPMA Solution Added (ml) |
| --- | --- |
| 0–30 | 418.58 |
| 30–60 | 269.80 |
| 60–90 | 153.90 |
| 90–120 | 80.56 |

-continued

| Time (min.) | Amount of DMAPMA Solution Added (ml) |
|---|---|
| 120–150 | 40.10 |
| 150–180 | 19.38 |
| 180–210 | 9.32 |
| 210–240 | 4.38 |

The totals added during the entire reaction were VP (216 grams), DMAPMA (54 grams) and water (1530 grams).

Additions of Lupersol 11 (t-butyl peroxypivalate, Atochem, NA) initiator were made at various intervals throughout the initial part of the reaction. Additions of 0.25 ml of the initiator were made at 0, 10, 40, 70, 100, 140 and 180 minutes. At 210 and 240 minutes, 0.25 ml of either VAZO 501 (4,4'-azobis(4-cyanovaleric) acid, Wako Pure Chemical Industries, Ltd, Japan) was added to complete the reaction of any residual vinylpyrrolidone monomer. For this purpose, the reaction was allowed to proceed for a total of 10 hours. During this final period the temperature was raised to 75° C. where it was maintained until the reaction was completed.

The product was discharged as a clear, moderately viscous, aqueous solution of a substantially homogeneous copolymer of VP and DMAPMA in an 80:20 weight ratio at a 15% solids level. The residual vinylpyrrolidone content was <0.1%.

The procedure described above can be repeated to provide optimized DMAPMA feeding schedules for any selected copolymer composition, and at any particular solids content, at a prescribed polymerization temperature, solvent level, and amount of initiator.

Table 1 below shows the advantageous physical properties of low viscosity and enhanced clarity for the homogeneous copolymer solution of the invention, as compared to non-homogeneous copolymer solutions of the same composition.

TABLE 1

| | Viscosity*** (cps) | Clarity+ (NTU) | Mol. Wt. |
|---|---|---|---|
| Homogeneous copolymer solution | 61,500 | 1.80* | 610,000 |
| Non-homogeneous copolymer solution | 150,000 | 14.15** | 620,000 |

+Hach; on 0.4% aqueous solution
*pH = 7.98
**pH = 7.44
***Brookfield viscosity, on 15% aqueous solution; Model RTV, 20 rpm, Spindle #7, 252° C.

HAIR STYLING COMPOSITIONS

The substantially homogeneous copolymer of the invention finds particular utility in multifunctional hair care products such as water-based, rinse-off hair styling and conditioning products, and in mousse hair care products. It may be included in such compositions as a concentrate, or as a gel, and applied as a self-actuated pump hair spray, or in an aerosol product with a propellant. Various actuator and packaging devices known in the art may be used therewith.

Such hair styling products have significantly improved hair holding (curl retention) and hair stiffness properties, while maintaining enhanced hair conditioning (detangling, flyaway and combability) properties, compared to non-homogeneously prepared copolymers of the same monomers, when formulated into hair styling compositions.

HAIR STYLING COMPOSITIONS OF INVENTION

| | Hair Styling Gel | Wt (g) |
|---|---|---|
| (a) | Homogeneous copolymer of VP/DMAPMA (80:20) (as 15% aqueous solution) | 5.00 |
| (b) | Hydroxyethyl cellulose (Natrosol ® 250 HHR-Aqulon) | 0.50 |
| (c) | Triethanolamine (99%) (TEA) | 0.20 |
| (d) | Deionized water | qs |

Preparation:
1. Heat (d) to 85° C.
2. Add (b) while mixing well.
3. Add (a) with rapid mixing.
4. Neutralize with (c).

| | Hair Styling Mousse | Wt (g) |
|---|---|---|
| (a) | Homogeneous copolymer of VP/DMAPMA (80:20) (as 15% aqueous solution) | 5.0 |
| (b) | Sodium cocoyl isothionate (Igepon ® AC-78 Rhone-Poulenc) | 0.75 |
| (c) | Emulsifying wax (Polowax ® A-31 Croda) | 0.15 |
| (d) | Propylene glycol, diazolidinyl urea, methyl paraben and propyl paraben (Germaben ® II - Sutton (ISP) | 0.25 |
| (e) | Dymel ® 152A (1,1-difluoroethane) | 4.00 |
| (f) | Hydrocarbon A-17 (n-butane) | 4.00 |
| (g) | Water | qs |

Preparations:
1. Add (a) to (g) while agitating and heating to 55–60° C.
2. A dd (b) while mixing at 55° C. Begin cooling.
3. Add (c) and mix rapidly.
4. Cool to 25° C. and add (d).
5. Charge into pressurized container and add (e) and (f).

Table 2 below demonstrates the advantageous curl retention property for a hair styling composition (gel) containing the homogeneous copolymer of the invention as compared to a non-homogeneous copolymer.

TABLE 2

CURL RETENTION PROPERTY

| Copolymer in Hair Styling Composition | Relative Curl Retention of Composition* |
|---|---|
| Homogeneous Copolymer | 116.9 |
| Non-homogeneous Copolymer | 95.3 |

*vs. standard at 90% RH and 90 min. duration

While the invention has been described with particular reference to certain embodiments thereof, it will be understood that changes and modifications may be made which are within the skill of the art. Accordingly, it is intended to be bound only by the following claims, in which:

What is claimed is:

1. A process for making clear, low viscosity aqueous solutions of a homogeneous copolymer of vinyl pyrrolidone (VP) and N-3,3-dimethylaminopropyl methacrylamide (DMAPMA), in the compositional range of 20–99% VP and 1–80% DMAPMA, by weight, having a weight average molecular weight of about 200,000 to about 1,500,000, a solids content of about 5–20%, and a viscosity of about 5,000 to 80,000 cps, by polymerization of the monomers in water in the presence of a radical initiator, which comprises:

(a) precharging a reactor with a predetermined amount of VP, and water, at a polymerization temperature of about 50–90° C., and (b) introducing DMAPMA into said reactor at a predetermined rate corresponding to the rate of disappearance of VP, over a given period of time.

2. A process according to claim 1 wherein the DMAPMA is introduced in water.

3. A process according to claim 1 wherein said weight ratio of VP:DMAPMA is about 50–95% to 5–50%.

4. A process according to claim 1 wherein said solids content is about 10–15%.

5. A process according to claim 4 wherein said viscosity is about 10,000 to 70,000 cps.

6. A process according to claim 1 which also includes the step of post-heating with additional radical initiator to reduce the residual VP content to <0.1%.

7. A process according to claim 1 wherein DMAPMA is introduced until substantially all the starting VP has been copolymerized to the desired copolymer.

8. A process according to claim 1 wherein the radical initiator is t-butylperoxy pivalate.

9. A process according to claim 6 wherein the additional radical initiator is 4,4'-azobis(4-cyanovaleric acid).

10. A process according to claim 1 wherein up to 10% of the DMAPMA is included in the precharge.

* * * * *